(12) United States Patent
Deal et al.

(10) Patent No.: US 7,141,050 B2
(45) Date of Patent: Nov. 28, 2006

(54) CATHETER WITH A PLURALITY OF WIRE GUIDE ACCESS PARTS

(75) Inventors: Stephen E. Deal, Charlotte, NC (US); David F. Waller, Charlotte, NC (US)

(73) Assignee: Wilson-Cook Medical Inc., Winston-Salem, NC (US)

( * ) Notice: Subject to any disclaimer, the term of this patent is extended or adjusted under 35 U.S.C. 154(b) by 76 days.

(21) Appl. No.: 10/688,846

(22) Filed: Oct. 17, 2003

(65) Prior Publication Data

US 2004/0133198 A1 Jul. 8, 2004

Related U.S. Application Data

(60) Provisional application No. 60/419,550, filed on Oct. 18, 2002.

(51) Int. Cl.
*A61B 18/18* (2006.01)
(52) U.S. Cl. .................. 606/47; 606/46; 604/508; 604/509; 604/510; 604/523
(58) Field of Classification Search .............. 606/47, 606/46; 604/523, 508, 509, 510, 103.04, 604/96.01, 102.01, 264, 533
See application file for complete search history.

(56) References Cited

U.S. PATENT DOCUMENTS

| | | | |
|---|---|---|---|
| 4,932,413 A | * | 6/1990 | Shockey et al. ............. 600/434 |
| 4,947,864 A | | 8/1990 | Shockey et al. |
| 5,163,950 A | * | 11/1992 | Pinchuk et al. ............. 606/192 |
| 5,336,184 A | | 8/1994 | Teirstein |
| 5,364,376 A | | 11/1994 | Horzewski et al. |
| 5,395,335 A | * | 3/1995 | Jang ..................... 604/102.02 |
| 5,409,012 A | * | 4/1995 | Sahatjian .................. 128/749 |
| 5,458,574 A | * | 10/1995 | Machold et al. ............. 604/101 |
| 5,547,469 A | * | 8/1996 | Rowland et al. ............. 604/22 |
| 5,554,118 A | | 9/1996 | Jang |

(Continued)

FOREIGN PATENT DOCUMENTS

WO WO 93 05841 4/1993

(Continued)

OTHER PUBLICATIONS

S. Sherman, M.D., "Wire-guided Sphincterotomy," The American Journal of Gastroenterology, 89(12):2125-2129 (1994).

(Continued)

*Primary Examiner*—Michael Peffley
*Assistant Examiner*—Alex Toy
(74) *Attorney, Agent, or Firm*—Brinks Hofer Gilson & Lione

(57) ABSTRACT

A physician access system comprising a catheter for use with an endoscope, the catheter including a wire guide lumen having a plurality of access ports disposed along an intermediate portion thereof to permit the insertion of a wire guide at different locations. The location of each access port corresponds to a specific length of the catheter exiting from the distal end of the endoscope. The access ports are located so that at least one of the access ports will be positioned near the endoscope handle when the distal end of the catheter, and any operational tool attached thereto, has been extended a short distance past the distal end of the endoscope. A physician may select the access port which best allows simultaneous control of the wire guide and the endoscope depending on the length of the catheter that the physician desires to have extend from the end of the endoscope.

15 Claims, 3 Drawing Sheets

U.S. PATENT DOCUMENTS

| | | | |
|---|---|---|---|
| 5,904,698 A * | 5/1999 | Thomas et al. | 606/159 |
| 5,971,983 A * | 10/1999 | Lesh | 606/41 |
| 5,980,483 A * | 11/1999 | Dimitri | 604/102.01 |
| 6,152,910 A * | 11/2000 | Agro et al. | 604/523 |
| 6,273,899 B1 * | 8/2001 | Kramer | 606/194 |
| 6,312,404 B1 | 11/2001 | Agro et al. | |
| 2002/0026149 A1 | 2/2002 | Agro et al. | |
| 2002/0049423 A1 | 4/2002 | Howell et al. | |
| 2002/0058905 A1 | 5/2002 | Madrid et al. | |

FOREIGN PATENT DOCUMENTS

| | | |
|---|---|---|
| WO | WO 98 52637 | 11/1998 |
| WO | WO 01 66178 | 9/2001 |

OTHER PUBLICATIONS

Wilson-Cook Medical, Inc. "Swenson Wire Guided Papillotomes/Sphincterotomes" Brochure.

* cited by examiner

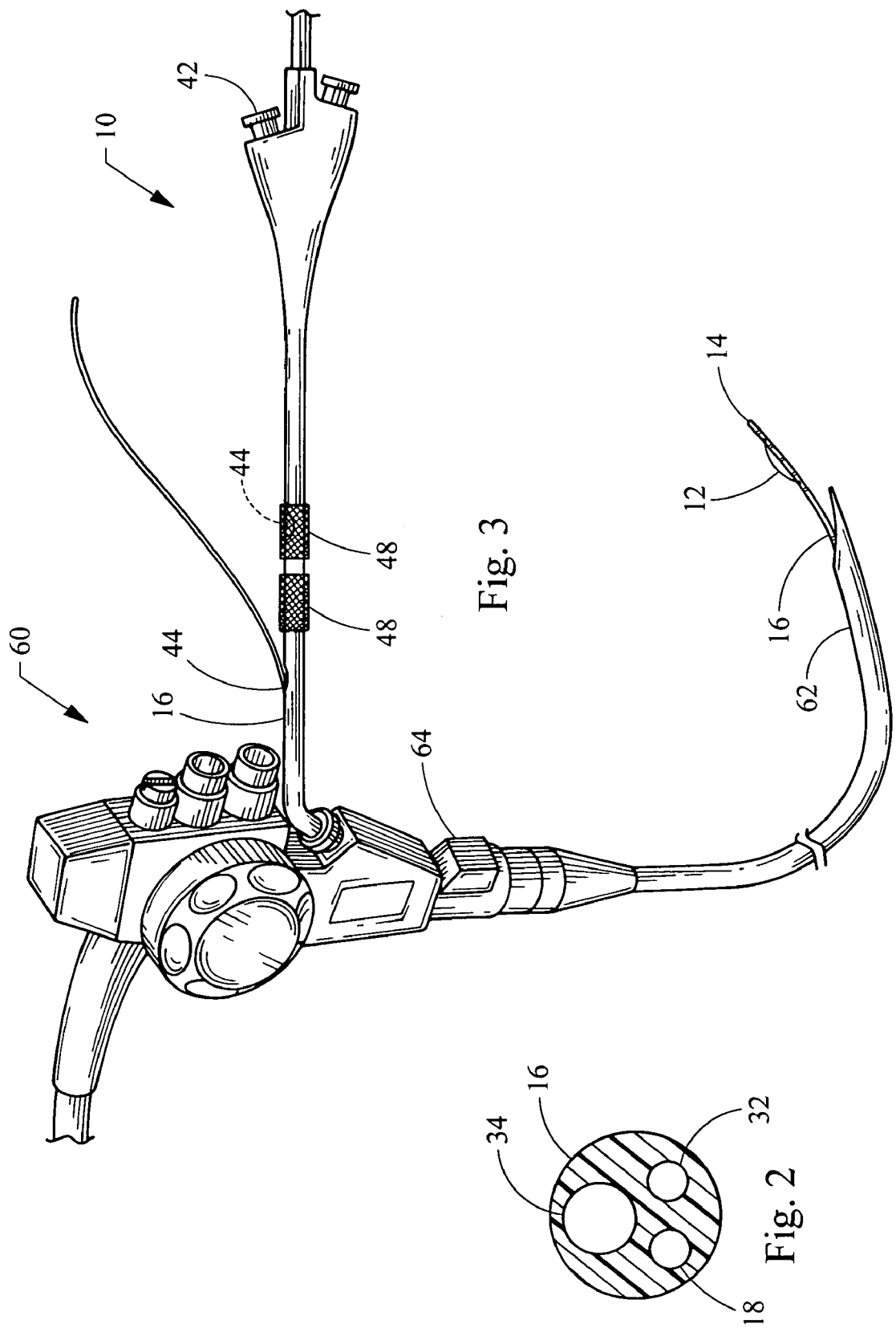

CATHETER WITH A PLURALITY OF WIRE GUIDE ACCESS PARTS

The present patent document claims the benefit of the filing date under 35 U.S.C. §119(e) of Provisional U.S. Patent Application Ser. No. 60/419,550, filed Oct. 18, 2002, which is hereby incorporated by reference.

The present invention relates generally to wire guided medical devices and, in particular, to medical catheters for use with endoscopes.

BACKGROUND OF THE INVENTION

Endoscopes are used in various medical procedures as a less invasive alternative to more traditional surgical operations. Typically, an endoscope is inserted into the patient through either a natural orifice in the body such as the oral cavity, or through an incision made in the skin of the patient, so as to gain access to an internal part of the patient's anatomy. Once the endoscope is positioned within the patient, the physician can view the diseased or damaged area of the anatomy through a series of lenses or optic fibers within the endoscope. These lenses or optic fibers likewise provide illumination to the targeted anatomical area.

The endoscope may also employ one or more extra channels through which operating instruments may be passed. Such operating instruments may include dilation balloons, irrigation catheters, electrosurgical probes, papillotomes, cutting forceps or snares, or tissue sampling devices. These extra channels through the endoscope may also be used for the delivery of fluids or gasses, or to provide suction to the targeted anatomical area. Some endoscopes also include operating handles having controls for manipulating the tip of the endoscope so as to permit the endoscope to be maneuvered through the patient's anatomy.

In endoscopic procedures employing an operating instrument passed through the endoscope, it is often necessary to pass a wire guide through the catheter of the operating instrument. For example, in ERCP procedures, an endoscope is inserted into the patient's mouth and through the esophagus, stomach, and duodenum until it reaches the area where the ducts of the biliary tree and the pancreas open into the duodenum. This area is called the papilla of Vater. The physician then utilizes the endoscope's optics to view and diagnose any problems in the liver, gallbladder, bile ducts, and pancreas. The physician may also inject dyes (contrast) through the channel of the endoscope. The dyes are visible with x-rays, and aid the physician in the diagnosis.

In some patients, the diagnosis reveals the presence of calculi in the common duct, which are typically formed by secretions and mineral deposits. The calculi can cause an interruption of liver bile flow into the duodenum, and can irritate the surrounding tissue, thereby further interrupting the flow of bile. Any such obstructions in the papilla of Vater are typically removed or otherwise alleviated with a papillotome. The papillotome comprises an electrically conductive cutting wire extending through a multi-lumen catheter, which is inserted through the channel of the endoscope. One lumen is utilized for passing the electrically conductive wire therethrough, while another lumen is utilized for extending a wire guide therethrough. The wire guide is used to position the papillotome at the proper anatomical location. The proximal end of the papillotome typically includes a manually operated handle attached to the cutting wire that permits the distal end of the catheter to be deflected. This is done so as to form a loop at the distal end of the cutting catheter to engage tissue and, more particularly, to engage the papilla so as to enlarge the opening thereat.

Medical catheters for use with endoscopes are typically longer than the overall length of the endoscope. For example, endoscopes for use in medical procedures of the type described above typically have an overall length of 150–160 cm. Medical catheters for use with these endoscopes, such as the papillotome described above, typically have an overall length of approximately 200 cm. The catheter is longer than the endoscope so as to permit the distal end of the catheter to extend a sufficient distance beyond the distal end of the endoscope to perform cannulation or other procedures. However, the additional length of the catheter relative to the endoscope creates certain problems, particularly with respect to the insertion and manipulation of a wire guide through the catheter.

For example, when the catheter is used to perform a medical procedure such as sphincterotomy, the distal end of the catheter is only extended a short distance beyond the distal end of the endoscope. In other words, only that portion of the distal end of the catheter that comprises the operational device, such as a cutting wire, is typically extended beyond the end of the endoscope. A substantial portion of the catheter that is adjacent to the catheter's handle therefore extends from the proximal end of the endoscope. As a consequence, the catheter's handle and the wire guide port, which is typically located near the catheter's handle, are spaced a substantial distance away from the endoscope. This spaced arrangement, however, makes it difficult for the physician to simultaneously insert or manipulate a wire guide inserted into the catheter and manipulate the endoscope. A physician will therefore usually elect to personally manipulate the endoscope, and rely on an assistant to manipulate the wire guide. This can be problematic because of the difficulty in issuing and/or following voice commands between the physician and the assistant in an accurate and timely manner.

Accordingly, there is a need for a wire guided medical catheter that permits the physician to simultaneously manipulate a wire guide inserted through the catheter and an endoscope.

Another problem with conventional medical catheters of the type described above is that it is often difficult to accurately determine how far the distal end of the catheter extends beyond the distal end of the endoscope. For example, it may be desirable to extend the distal end of the catheter a fixed distance beyond the end of the endoscope so as to enable an operational tool on the distal end of the catheter to perform a specific medical procedure. This is ordinarily accomplished by observing the length of the proximal end of the catheter extending from the proximal end of the endoscope, and then estimating the length of the distal end of the catheter extending beyond the distal end of the endoscope. However, because conventional medical catheters are substantially longer than the endoscopes in which they are typically used, such visual estimates are difficult to make with any accuracy.

Accordingly, there is a need for a wire guided medical catheter that enables the physician to quickly and accurately determine the length of the distal end of the catheter extending beyond the distal end of the endoscope.

SUMMARY OF THE INVENTION

The physician access system according to the present invention comprises a catheter for use with an endoscope. The catheter includes a wire guide lumen having a plurality of access ports disposed along an intermediate portion thereof to permit the insertion of a wire guide at different locations. The location of each access port corresponds to a specific length of the catheter exiting from the distal end of the endoscope. In particular, the access ports are located so that at least one of the access ports will be positioned near the endoscope handle when the distal end of the catheter, and any operational tool attached thereto, has been extended a short distance past the distal end of the endoscope. Accordingly, the physician may select the access port which best allows simultaneous control of the wire guide and the endoscope depending on the length of the catheter that the physician desires to have extend from the end of the endoscope.

In one embodiment of the present invention, the physician access system comprises a triple lumen sphincterotome for use in cannulation of the ductal system and for sphincterotomy. The sphincterotome has an overall length of approximately 200 cm, and includes an electrically conductive wire extending through one of the lumens in the catheter. The proximal end of the conductive wire is attached to a handle. A short portion of the distal end of the conductive wire is connected to the exterior of the distal end of the catheter such that manipulation of the handle bends the distal tip of the catheter to cause the conductive wire to arch outwardly from the surface thereof to perform cutting procedures.

The second lumen of the catheter provides a passageway for the injection of fluids or gases, and the third lumen provides a passageway for a wire guide. First and second ports are affixed to the proximal end of the catheter near the handle, and provide access to the second and third lumens, respectively. A pair of intermediate access ports are disposed along an intermediate portion of the catheter, and permit additional points of access to the wire guide lumen. The intermediate access ports are located a predetermined distance from the proximal and distal ends of the catheter, and correspond to a predetermined length of the distal end of the catheter extending beyond the distal end of the endoscope when the intermediate access ports are positioned adjacent to the proximal end of the endoscope. When not in use, each of the intermediate access ports is closed with a piece of shrink tubing (or other type of sleeve) that is slidably disposed about exterior of the catheter.

BRIEF DESCRIPTION OF THE DRAWINGS

FIG. 2 is a cross-sectional view taken along line 2—2 of FIG. 1.

FIGS. 3 and 3A are illustrations of the embodiment of the physician access system shown in FIG. 1 inserted through an endoscope.

DESCRIPTION OF THE INVENTION

Figure 1:
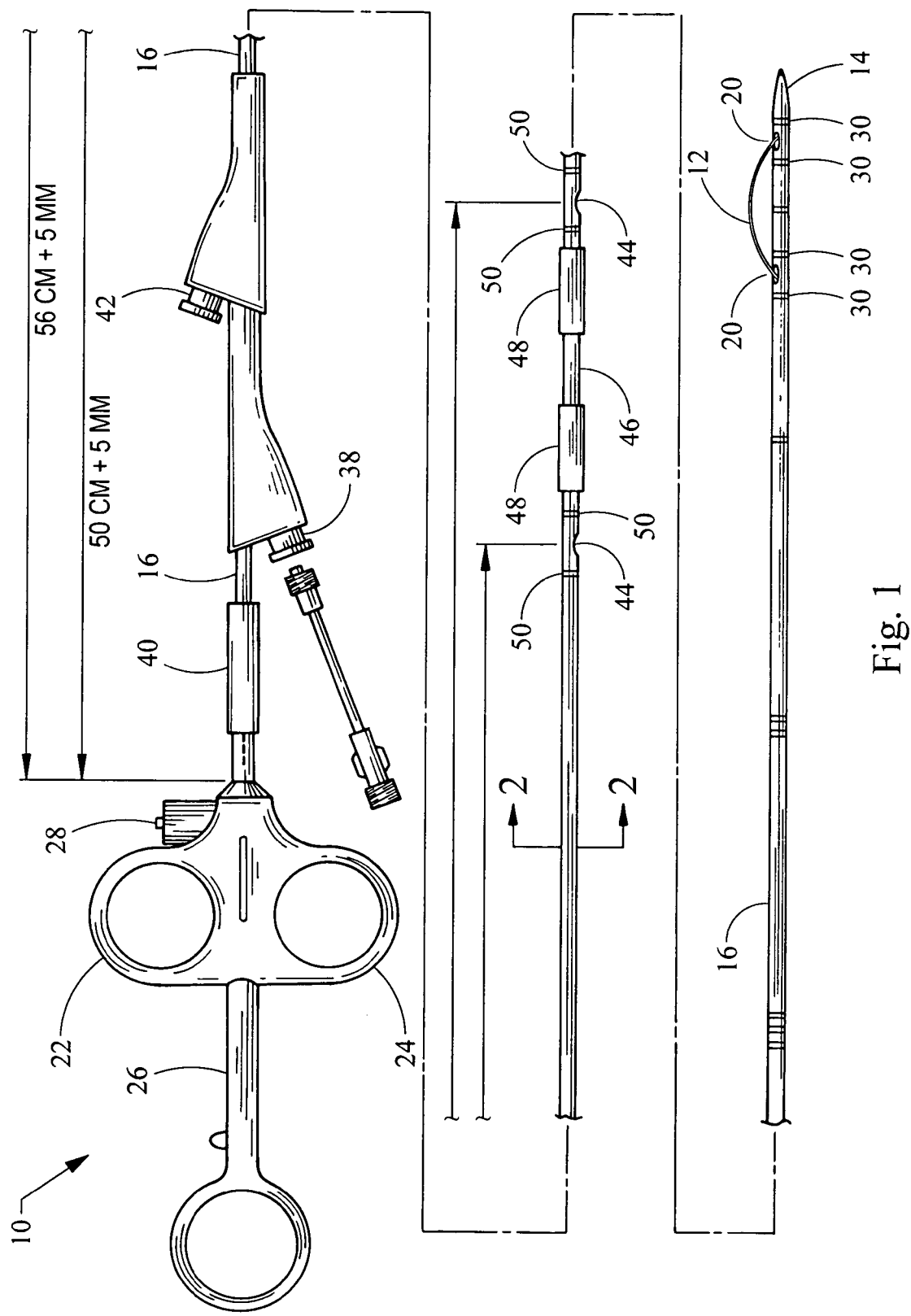
FIG. 1 is an illustration of one embodiment of the physician access system according to the present invention.

The physician access system according to the present invention comprises a wire guided catheter or the like for use with an endoscope. Referring to FIG. 1, a triple lumen sphincterotome 10 according to the present invention is shown. The sphincterotome 10 is used in combination with an endoscope 60 (see FIG. 3) for cannulation of the ductal system and for sphincterotomy. Specifically, the sphincterotome 10 is used to cut tissue, and more particularly, is used to sever the papilla with an electrically energizable compression member 12 externally positioned about the distal end 14 of the catheter or elongate member 16. The compression member 12, typically comprising a metallic, electrically conductive wire, tube cannula, or braid, is internally anchored in a first passage or lumen 18 of the elongate member 16 at the distal end 14, and externally exits the elongate member for a short distance via distal side ports 20. The compression member 12 extends almost along the entire length of the first passage 18 of the elongate member 16, and is attached to a manually operated, three-ring catheter handle 22.

As shown, the catheter handle 22 is in a non-actuated position. The catheter handle 22 is actuated by pulling on handle part 24 in a proximal direction with respect to handle part 26. This causes the proximal end of the compression member 12, which is attached to the actuated handle part 24, to exert a pulling force on the distal end 14 of the elongate member 16 so as to fold it back upon itself, thereby forming a distal loop with the externally positioned compression member 12. While in this position, tissue can be electrosurgically severed with the externally positioned compression member 12. More particularly, the papilla is severed by positioning the compression member 12 against the tissue and then supplying electrical energy to the compression member via electrical terminal 28 disposed on the catheter handle 22.

As best seen in FIG. 1, markings 30 on the distal end 14 of the elongate member 16 assist in identifying the ends and the middle of the compression member 12. These markings 30 typically have different colors to aid in their identification, particularly when only one of the markings 30 may be visual through the endoscope. For example, the markings 30 near the distal end of the compression member 12 are green in color, whereas the markings 30 near the proximal end of the compression member 12 are blue in color.

Referring to FIG. 2, the elongate member 16 comprises three separate lumens or passages disposed along the length thereof. As explained above, the compression member 12 is disposed within the first lumen or passage 18. The second lumen or passage 32 provides a passageway for the injection of fluids or gases, and the third lumen or passage 34 provides a passageway for a wire guide 36. A first side port 38 is affixed to the proximal end 40 of the elongate member 16 near the catheter handle 22 and provides access to the second passage 32. In other words, the first side port 38 provides an opening through which fluids or gasses can be injected into and through the second passage 32. A second side port 42 is similarly affixed to the proximal end 40 of the elongate member 16 near the catheter handle 22 (although a short distance distal of the first side port 38) and provides access to the third passage 34. In other words, the second side port 42 provides an opening through which a wire guide can be inserted into and passed through the third passage 34. In the embodiment shown, the third passage 34 is larger than the first and second passages 18 and 32 to accommodate the larger diameter of a standard wire guide 36.

Referring to FIG. 1, a pair of intermediate access ports 44 are disposed along an intermediate or central portion 46 of the elongate member 16, and provide additional points of access to the third passage 34 (i.e., the wire guide lumen). The intermediate access ports 44 are each located a predetermined distance from both the proximal end 40 and the distal end 14 of the elongate member 16. More specifically, and as best seen in FIG. 3, location of the each of the intermediate access ports 44 correspond to a predetermined length of the distal end 14 of the elongate member 16 extending beyond the distal end 62 of the endoscope 60. In other words, the intermediate access ports 44 are located along the length of the elongate member 16 at positions that result in at least one of the intermediate access ports 44 being near the endoscope 60 when the distal end 14 of the elongate member 16 has been extended beyond the distal end 62 of the endoscope 60 a distance that is optimum for performing certain medical procedures.

For example, a physician desiring to perform sphincterotomy will typically extend the distal end 14 of the elongate member 16 beyond the distal end 62 of the endoscope 60 only a distance that is sufficient to permit manipulation and operation of the compression member 12. Extending the distal end 14 of the elongate member 16 further will only move the compression member 12 out of the physician's field of the view (through the endoscope 60). However, and as best seen in FIG. 3, the elongate member 16 typically has an overall length that is substantially greater than the length of the endoscope 60. This additional length is necessary because the distal end 14 of the elongate member 16 is often needed for other procedures such as cannulation. In any event, when the elongate member 16 is in the proper position for performing sphincterotomy, the second side port 42 will be spaced a substantial distance away from the handle 64 of the endoscope 60. As a result, the physician may have difficulty in inserting a wire guide 36 into the second side port 42 and through the third passage 34 (i.e., the wire guide lumen), and may likewise have difficulty in manipulating a wire guide 36 that has already been threaded through the second port 42. The physician may therefore elect to insert the wire guide 36 through one of the intermediate access ports 44.

Figure 3A:
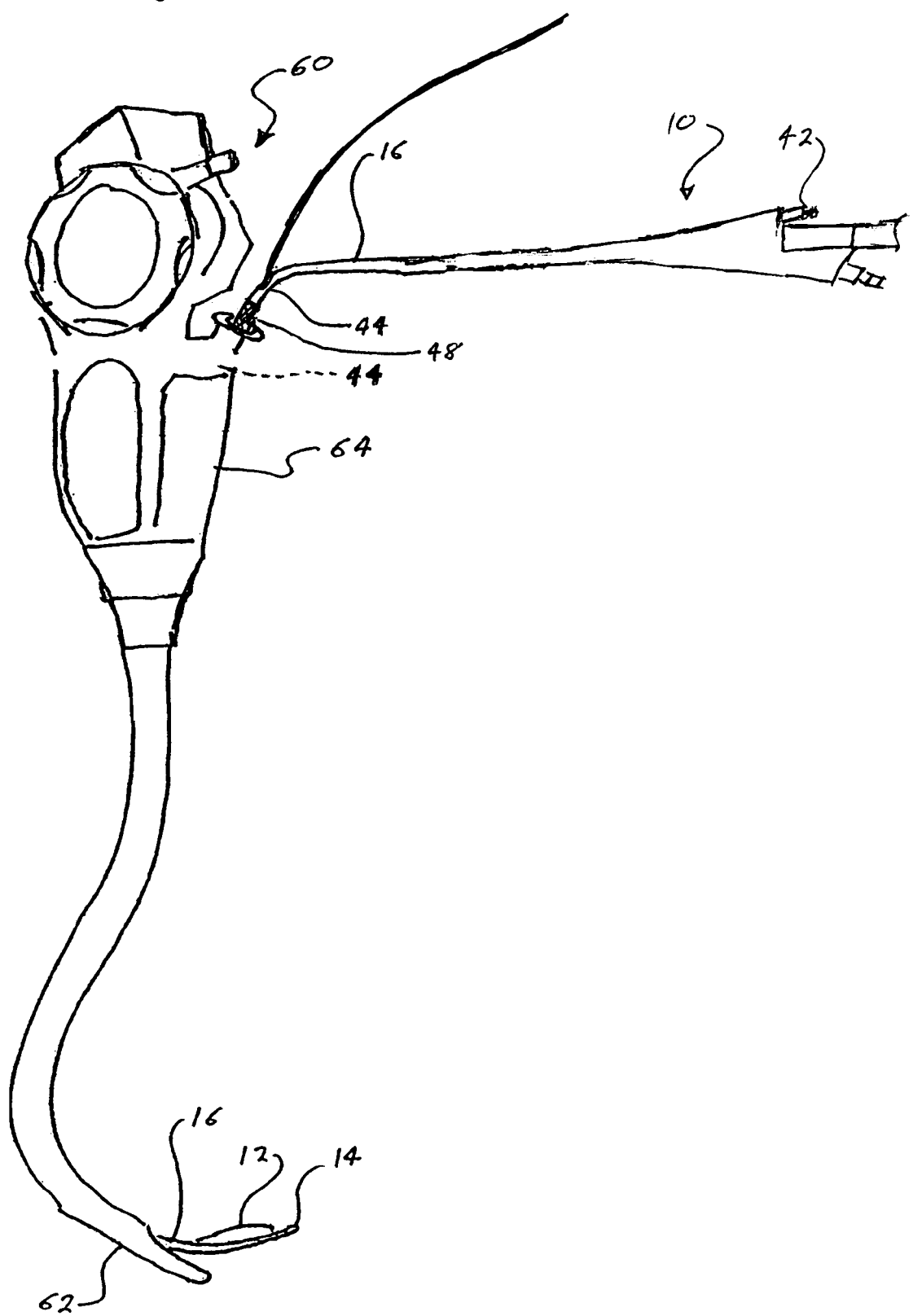

For example, the physician may elect to use the more distal of the intermediate access ports 44, which is, as shown in FIG. 3, the closer of the two intermediate access ports 44 to the endoscope. Insertion of the wire guide 36 through this intermediate access port 44 permits the physician to simultaneously manipulate both the endoscope 60 and the wire guide 36. If, on the other hand, the physician desires to extend the distal end 14 of the elongate member 16 an additional distance beyond the distal end 62 of the endoscope, the more distal intermediate access port 44 may end up inside the handle 64 of the endoscope 60. If so, then the more proximal of the intermediate access ports 44 should still be accessible for insertion of the wire guide 36 (see FIG. 3A).

When not in use, each of the intermediate access ports 44 is closed with a short length of shrink tubing 48 (or other type of sleeve) that is slidably disposed about exterior surface of the elongate member 16. When the physician desires to access one of the intermediate access ports 44, the shrink tubing 48 is slid along the length of the elongate member 16 so as to expose the desired the intermediate access port 44. The shrink tubing 48 has an inside diameter that closely corresponds with the outside diameter of the elongate member 16 so as to create a frictional force between these components sufficient to prevent inadvertent or unintended sliding of the shrink tubing 48 along the length of the elongate member 16. A tight fitting relationship between these two components also prevents fluids or other contaminants from inadvertently entering or exiting through the intermediate access ports 44.

In addition, the shrink tubing 48 has a color that contrasts with that of the elongate member 16 so as to permit the location of the shrink tubing 48 to be readily identified. Similarly, the elongate member 16 includes markings 50 adjacent to each of the intermediate access ports 44 to likewise permit the location of each of the intermediate access ports 44 to be readily identified, and to permit rapid verification as to whether the intermediate access ports 44 are open or closed.

As explained above, the location of each of the intermediate access ports 44 along the length of the elongate member 16 corresponds to one or more specific procedures that are to be performed with the sphincterotome 10, and to the appropriate length of the elongate member 16 required to extend beyond the distal end 62 of the endoscope 60 to perform those procedures.

In addition to the above, the location of each of the intermediate access ports 44 also provides reference points for the physician when inserting the elongate member 16 of the sphincterotome 10 into and through the endoscope 60. For example, the physician can use the location of each of the intermediate access ports 44 to determine how far the distal end 14 of the elongate member 16 extends beyond the distal end 62 of the endoscope 60. This eliminates the need for the physician to look thought the endoscope 60 to determine when the distal end 14 of the elongate member 16 has passed out through the distal end 62 of the endoscope 60. Instead, the physician make this determination by comparing the location of the intermediate access ports 44 relative to the handle 64 of the endoscope 60.

In the embodiment shown in FIG. 1, the elongate member 16 has an overall length of approximately 200 cm. Each of the intermediate access ports 44 are located approximately 50 cm and 56 cm, respectively, from the proximal end 40 of the elongate member 16 (i.e., where the elongate member 16 is connected to the catheter handle 22). These access ports are likewise located approximately 150 cm and 144 cm, respectively, from the distal end 14. Of course, it should be understood that any number of intermediate access ports 44 may be employed at various locations along the length of the elongate member.

Although the specific embodiment discussed above is directed to a sphincterotome, it should be understood that the physician access system of the present invention will find application in other types of wire guided devices. For example, the physician access system could be incorporated into dilation balloons, irrigation catheters, electrosurgical probes, cutting forceps or snares, or tissue sampling devices. Accordingly, it should be understood that the exact location of each of the intermediate access ports may vary depending on the type of wire guided device being employed, the type of medical procedures to be performed with the wire guided device, the overall length of the endoscope, and the length of that portion of the wire guided device required to extend beyond the endoscope to perform these procedures.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention.

The invention claimed is:

1. A catheter comprising:
   a catheter shaft of sufficient length to perform an endoscopic procedure in the biliary system and having a proximal end, a distal end, and a wire guide lumen extending through the shaft between a proximal wire guide port and a distal wire guide port; and
   a plurality of intermediate wire guide access ports located a not insubstantial distance distal of the proximal wire guide port and a not insubstantial distance proximal of the distal wire guide port,
   wherein a plurality of sleeves are slidably disposed along the catheter shaft, the plurality of sleeves comprising a first sleeve that is movable between a first position restricting access from exterior of the catheter through a first intermediate wire guide access port and a second position wherein access is not restricted through the first intermediate wire guide access port, and further comprising a second sleeve that is movable between a first position restricting access from exterior of the catheter through a second intermediate wire guide access port and a second position wherein access is not restricted through the second intermediate wire guide access port.

2. The catheter of claim 1, further comprising a plurality of markers adjacent the plurality of intermediate wire guide access ports.

3. The catheter of claim 1, wherein the catheter is adapted for use with an endoscope having a working channel extending between a distal port and a proximal port and wherein the first and second intermediate wire guide access ports are each accessible outside the endoscope when the catheter is positioned through the working channel such that the distal end of the catheter and the distal port of the working channel are substantially aligned.

4. The catheter of claim 1, wherein the first and second intermediate wire guide access ports are located at least about 150 cm from the distal end of the catheter shaft.

5. The catheter of claim 1, wherein at least one of the first and second intermediate wire guide access ports is located approximately 50 cm to 56 cm from the proximal end of the catheter shaft.

6. The catheter of claim 1, wherein the first and second intermediate wire guide access ports are each located in a spaced apart fashion on the catheter shaft within the range of about 50 cm to 56 cm from the proximal end of the catheter shaft.

7. The catheter of claim 1, wherein at least one of the first and second intermediate wire guide access ports is located approximately 144 cm to 150 cm from the distal end of the catheter shaft.

8. The catheter of claim 1, wherein the first and second intermediate wire guide access ports are each located in a spaced apart fashion on the catheter shaft within the range of about 144 cm to 150 cm from the distal end of the catheter shaft.

9. The catheter of claim 1, the catheter shaft further comprising a proximal half and a distal half, wherein the first and second intermediate wire guide access ports are each located in a spaced apart fashion on the proximal half of the catheter shaft.

10. A sphincterotome comprising:
    a catheter shaft having a proximal end and a distal end;
    a plurality of catheter lumens, including a lumen providing a passageway for injecting substances, a lumen including an electrically energizable compression member for cutting tissue, and a wire guide lumen extending from a proximal wire guide access port near the proximal end of the sphincterotome to a distal wire guide access port near the distal end of the sphincterotome; and
    a plurality of intermediate wire guide access ports located between and spaced apart from the proximal end and the distal end,
    wherein the sphincterotome is adapted for use with an endoscope having a working channel extending between a distal port and a proximal port and wherein the plurality of intermediate wire guide access ports are accessible outside the endoscope when the sphincterotome is positioned through the working channel such that the distal end of the catheter shaft and the distal port of the working channel are substantially aligned, further wherein one or more of the plurality of intermediate wire guide access ports are each configured to be disposed within the working channel when the distal end of the catheter shaft is extended distally past the distal port of the working channel.

11. The sphincterotome of claim 10, further comprising at least one slidable tube for allowing and restricting access to at least one of the plurality of intermediate wire guide access ports.

12. The sphincterotome of claim 10, wherein the electrically energizable compression member for cutting tissue has a portion that is external of the catheter shaft and wherein at least one of the plurality of intermediate wire guide access ports is near a handle of the endoscope when the sphincterotome is positioned inside the endoscope working channel and when the external portion of the compression member is outside of and adjacent the endoscope working channel distal port.

13. A method comprising the steps of:
    advancing a sphincterotome having a proximal end, a distal end, and a plurality of intermediate wire guide access ports located a not insubstantial distance distal of the proximal end and a not insubstantial distance proximal of the distal end into an endoscope having a handle; and
    while a first intermediate wire guide access port of the plurality of intermediate wire guide access ports is positioned near the handle of the endoscope, sliding a first tube disposed along the sphincterotome to allow access to the first intermediate wire guide access port and performing a sphincterotomy.

14. The method of claim 13, while the first intermediate wire guide access port of the plurality of wire guide access ports is near the handle of the endoscope, further comprising the step of advancing a wire guide through the first intermediate wire guide access port.

15. A sphincterotome comprising:
    a catheter shaft having a proximal end and a distal end;
    a plurality of catheter lumens, including a lumen providing a passageway for injecting substances, a lumen including an electrically energizable compression member for cutting tissue, and a wire guide lumen extending from a proximal wire guide access port near the proximal end of the sphincterotome to a distal wire guide access port near the distal end of the sphincterotome; and
    a plurality of intermediate wire guide access ports located between and spaced apart from the proximal end and the distal end,
    wherein the sphincterotome is adapted for use with an endoscope having a working channel extending between a distal port and a proximal port and wherein the plurality of intermediate wire guide access ports are accessible outside the endoscope when the sphincterotome is positioned through the working channel such that the distal end of the catheter shaft and the distal port of the working channel are substantially aligned, the sphincterotome further comprising at least one slidable tube for allowing and restricting access to at least one of the plurality of intermediate wire guide access ports.

* * * * *

UNITED STATES PATENT AND TRADEMARK OFFICE
CERTIFICATE OF CORRECTION

| | | |
|---|---|---|
| PATENT NO. | : 7,141,050 B2 | Page 1 of 1 |
| APPLICATION NO. | : 10/688846 | |
| DATED | : November 28, 2006 | |
| INVENTOR(S) | : Stephen E. Deal et al. | |

It is certified that error appears in the above-identified patent and that said Letters Patent is hereby corrected as shown below:

On the Title Page

Item (54), replace "GUIDE ACCESS PARTS" with --GUIDE ACCESS PORTS--.

Lines 1-2

Column 1, in the title, replace "GUIDE ACCESS PARTS" with --GUIDE ACCESS PORTS--.

Signed and Sealed this

Thirtieth Day of March, 2010

David J. Kappos
*Director of the United States Patent and Trademark Office*